United States Patent [19]
Prause et al.

[11] Patent Number: 5,461,920
[45] Date of Patent: Oct. 31, 1995

[54] WHOLE-BODY TEST SYSTEM WITH A TEST PROBE MOUNT DESIGNED ESPECIALLY AS A ROTOR WHICH IS MOUNTED ON A VERTICALLY ADJUSTABLE SUPPORT PLATFORM AND HAS A TEST-PIECE MANIPULATOR

[75] Inventors: Reinhard Prause, St. Augustin; Ottokar Patzke, Erfstadt-Lieblar; Reinhard Pawelletz, Dusseldorf; Bernhard Harbach, Erftstadt-Friesheim, all of Germany

[73] Assignee: Krautkramer GmbH & Co., Germany

[21] Appl. No.: 75,553

[22] PCT Filed: Dec. 18, 1991

[86] PCT No.: PCT/DE91/00989

§ 371 Date: Feb. 2, 1993

§ 102(e) Date: Feb. 2, 1993

[87] PCT Pub. No.: WO92/11533

PCT Pub. Date: Jul. 9, 1992

[30] Foreign Application Priority Data

Dec. 20, 1990 [DE] Germany .................. 40 40 870.1

[51] Int. Cl.[6] .................................................. G01N 29/22
[52] U.S. Cl. ...................................... 73/622; 73/1 DV
[58] Field of Search .............................. 73/1 DV, 622, 73/620

[56] References Cited

U.S. PATENT DOCUMENTS

| | | | |
|---|---|---|---|
| 3,371,524 | 3/1968 | Wloszek | 73/622 |
| 4,052,887 | 10/1977 | Sheridan et al. | 73/622 |
| 4,404,853 | 9/1983 | Livingston | 73/622 |
| 4,567,747 | 2/1986 | Matay | 73/1 DV |
| 4,660,419 | 4/1987 | Derkacs et al. | 73/622 |
| 4,744,251 | 5/1988 | Shirasu et al. | 73/622 |
| 4,905,516 | 3/1990 | Wölfl | 73/622 |

OTHER PUBLICATIONS

J. Krautkramer & H. Krautkramer, *Ultrasonic Testing of Materials*, pp. 439–457 (3d ed. 1983).

*Primary Examiner*—Hezron E. Williams
*Assistant Examiner*—Rose M. Finley
*Attorney, Agent, or Firm*—Eckert Seamans Cherin & Mellott

[57] ABSTRACT

In the whole-product ultrasonic inspection system proposed, a test head mount, having an axis of rotation, is mounted on a height-adjustable test bench. A test-piece, manipulator having an axis of rotation, is also mounted on the test bench. The test head mount axis and the test-piece manipulator axis are parallel to each other. A guideway is coupled between the test bench and the test head mount or the test-piece manipulator. The guideway runs in a direction that is orthogonal to the test head mount axis and the test-piece manipulator axis. The guideway is arranged such that the test-piece manipulator can move relative to the test head mount between a test position in which the test head mount axis and the test-piece manipulator axis coincide and a service position in which an object to be tested can be received by the test head mount.

9 Claims, 2 Drawing Sheets

WHOLE-BODY TEST SYSTEM WITH A TEST PROBE MOUNT DESIGNED ESPECIALLY AS A ROTOR WHICH IS MOUNTED ON A VERTICALLY ADJUSTABLE SUPPORT PLATFORM AND HAS A TEST-PIECE MANIPULATOR

BACKGROUND OF THE INVENTION

1. Field of the Invention

The invention pertains to an ultrasonic whole-body test system with a test probe mount designed especially as a rotor which is mounted on a vertically adjustable support platform and has a test-piece manipulator.

2. Prior Art

The term "whole-body test system" refers to ultrasonic test systems which are suitable for testing pipes, rods or other material with a regular polygonal profile and in which the test piece is scanned along a helical path with ultrasound. The test piece at this time moves in the direction of its longitudinal axis relative to the test probe mount. The test piece is either additionally rotated about its own longitudinal axis while the test probe mount remains stationary or the test probe mount is designed as a rotor which rotates about the axis of the object to be tested. Such test systems are described, for instance, in J. and H. Krautkrämer "Werkstoffprüfung mit Ultraschall" (Testing industrial materials with ultrasound), 4th edition, pages 442–461.

A test-piece manipulator allows test pieces (calibration standards) to be positioned precisely in the whole-body test system. Test pieces with the corresponding test-piece manipulator are the standards for the adjustment of ultrasonic test systems of the type under discussion here; with them the mechanical and electronic features of the test are set. Test pieces usually have several types of defects, depending on the test function. These defects are incorporated in different positions on the circumference and length of the test piece. To be able to detect all such defects (standard defects), it must be possible, on the one hand, to move the test piece into each position in its longitudinal axis relative to the test probe mount by means of the manipulator. On the other hand, it must be possible to rotate the test piece about its longitudinal axis and to perform oscillation movements, if necessary.

Standards and, in some cases, delivery contracts prescribe the intervals at which a whole-body test system must be tested to maintain predetermined production quality. The testing and adjusting are necessary, for example, because the probes become contaminated or worn during operation. To obtain the same electrical displays for the same defects in all cases, it may be necessary to adjust the amplification using the corresponding test piece.

This type of testing and adjustment of a whole-body test system always means a loss of production. Therefore, an effort must be made to keep the adjusting and testing times as short as possible. To accomplish this, it is necessary to change test pieces quickly and with the greatest possible automation.

In the practical course of an adjustment of a whole-body test system, the test probe mount is generally moved from the test position into a service position; this is usually performed horizontally. In this position, a test piece is moved into the probe mount by means of the test-piece manipulator.

Setting a test system with the previously known test-piece manipulator and the accompanying test pieces requires a relatively great amount of time. In each case a test piece must be mounted, the test-piece manipulator for the testing purpose in each case must be aligned axially with the test probe mount and relative movements must be carried out.

SUMMARY OF THE INVENTION

Proceeding on the basis of this state of the art, the goal of the invention was to modify a test system with a test-piece manipulator of the type discussed here in such a way that the adjusting and testing are essentially mechanized.

According to the invention, therefore, the test-piece manipulator and the test probe mount are mounted on the vertically adjustable support platform. A separate height adjustment mechanism is therefore not required. Furthermore, the bringing of the test probe mount into the path of the test-piece manipulator or, vice versa, the bringing of the test-piece manipulator into the testing line which is the axis of an object being tested in the test probe mount is thus simplified and can be precisely predetermined, so that either the test-piece manipulator or the test probe mount is mounted on the support platform by a longitudinal guide so that displacement transversely to the axis of the test-piece manipulator or the object being tested can take place. Alternatively the test-piece manipulator is mounted on a swivel arm which is attached to the vertically adjustable support platform. The swivel arm is operable to swivel about a swiveling axis. The swiveling axis is parallel to and located the same distance from the axis of the test-piece manipulator and the axis of an object being tested. The swivel arm is operable to swivel between two positions, in a first swivelled position the axis of the test-piece manipulator and the testing line coincide. In a second swivelled position the test-piece manipulator is in the rest and service position. The swivel arm can also be fitted with adjustable stops which assure that the test-piece manipulator is located properly when it is swiveled into each of the two positions.

Thus, the invention makes it possible to align the axes of the test-piece manipulator and the test probe mount rapidly because this alignment is done mechanically and therefore can be performed automatically in certain time intervals, e.g. controlled by a computer. The time required to prepare for actual tests is reduced in every case. The test-piece manipulator need not yet be aligned in any way; rather a test piece which is located on the test-piece manipulator can be pushed without additional adjusting measures into the test probe mount which, for example, is a rotor. The only criterion which distinguishes the individual test pieces from one another in such an arrangement is then the diameter of the test pieces. Expressed in other terms, for example, a test probe mount for the segment dipping technique must be set in such a way that the test piece is registered, or the sealing rings in the case of a test probe mount in the form of a rotor must be correspondingly designed so that the test piece can be moved in and adequately sealed.

This makes the following innovative adjustment of the whole-body test system possible: departing from previous practice in which the test piece has the same contour as the objects being tested, i.e. the pipes or rods to be tested, it is sufficient to hold a supply of test pieces in reserve in graduated diameters, e.g. 20 mm, 25 mm, 30 mm etc., and for products to be tested for intermediate values to extrapolate according to a predetermined table. Thus, for instance, a pipe with an outside diameter of 72 mm from production can be tested by using a test piece with an outside of diameter 70 mm and the adjustment can be found by extrapolation. The extrapolation is possible on the basis of the data from previously performed comparative measurements of pipes, e.g., the diameters of 80 mm and 70 min. In this way the inventory of test pieces can be considerably reduced and thus the mechanical process is also simplified.

Various design possibilities are available for the longitudinal guide. For example, it can be realized by rails which are mounted horizontally and on which the manipulator is mounted so as to slide with respect to the test probe mount (held stationary on the support platform). In another version, the manipulator can be attached to a vertical lifting device which forms a vertically running longitudinal guide. In both cases in a modified version the test-piece manipulator can also be firmly connected to the support platform and the test probe mount can be attached on rails on the lifting device and installed with the ability to move in relation to the test-piece manipulator.

It has been found to be very advantageous to attach the test-piece manipulator to the lifting platform via a second axial longitudinal guide. With this additional longitudinal guide, the test-piece manipulator can be moved parallel to the axial direction of the object being tested. In the test position it is possible in this way to move the test piece axially back and forth relative to the test probe mount, and thus to introduce the test piece into the test probe mount and withdraw it.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

The figures show a whole-body test system with a rotor 20. The rotor is mounted on a vertically adjustable support platform 22 whose surface is denoted by 24; it is horizontal and flat. The rotor 20 is rotated about a rotor axis 26 by devices not shown here. This axis coincides with the testing line of the whole-body test system or the axis of an object being tested 28.

Figure 1:
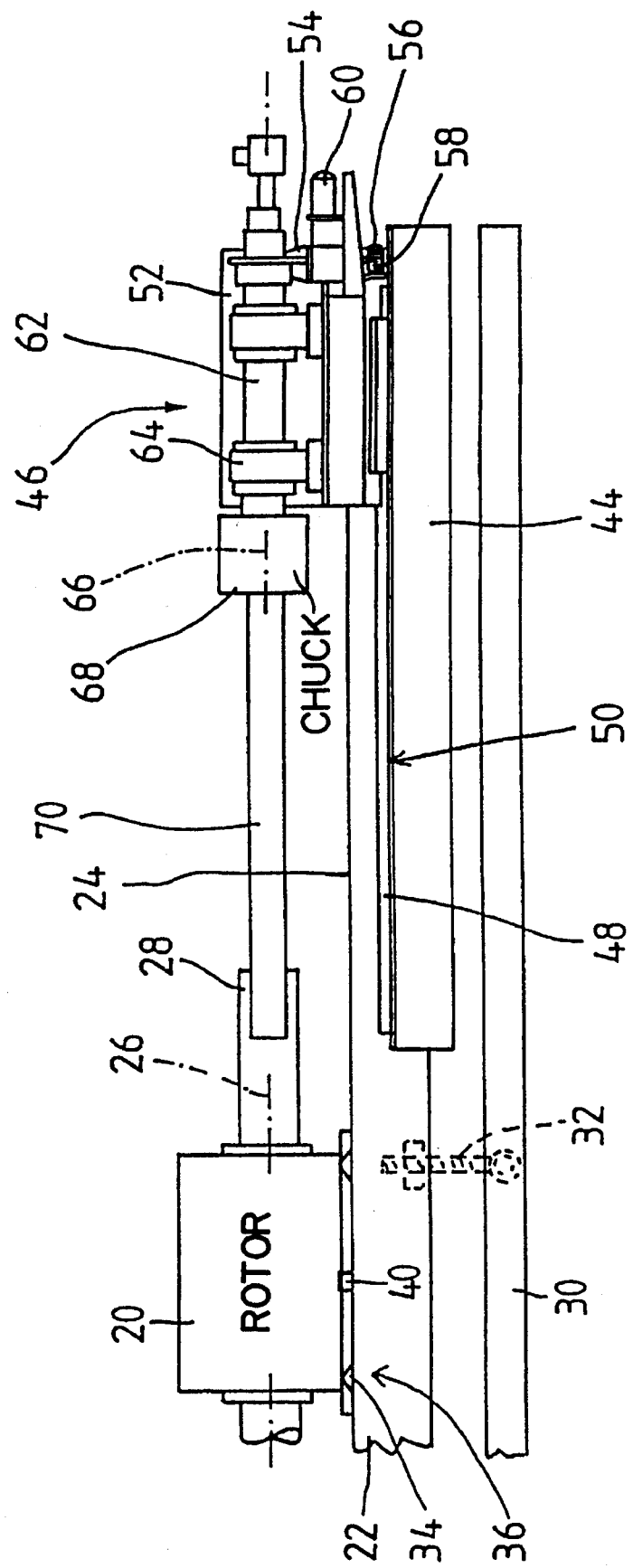
FIG. 1 is a side view of a test system of the type under discussion here, with the test probe mount designed as a rotor; the service position is shown with a test piece and a test-piece manipulator visible.

The support platform 22 is in turn supported on a base frame 30 and can be moved up and down by motor via a lifting-moving device 32. In the version shown the lifting-moving device 32 has several motor-driven spindles of which one is shown in FIG. 1. As FIG. 2 shows they are rotationally connected with one another.

The rotor 20 is mounted on rails 34 which form a first longitudinal guide 36. The rails 34 are designed as precision rails and attached directly on the surface 24 of the support platform 22. They extend at right angles to the rotor axis 26 (testing line). They are designed in such a way that the rotor 20 can be moved between the test position indicated by solid lines (FIG. 2) and the service and adjustment position indicated by broken lines transversely to the plane of FIG. 1. For the reciprocating motion of the rotor 20 on the rails 34, a drive motor 38 is provided which drives a pinion which engages a rack running parallel to the rails 34. Adjustable stops 40, 42 are assigned to the first longitudinal guide 36 for the test position or the service and adjustment position. They assure that the rotor occupies the correct position in each case. Alternatively adjustable stops can be coupled to the support platform.

A bracket 44 is flanged onto the support platform 22, whose surface lies in the plane of the surface 24. This bracket 44 carries the test-piece manipulator 46. For this purpose, rails 48 are attached to the bracket 44 which run parallel to the rotor axis 26 (testing line) and form a second longitudinal guide 50. A motor-driven sled 52 on these rails holds the test-piece manipulator 46. A motor drive is provided for moving the sled 52 in the second longitudinal guide 50 which corresponds to the above discussed motor drive of the rotor 20 on the first longitudinal guide 36: a servo drive motor 54 is attached on the sled 52 so as to drive a pinion 56 which in turn engages a rack 58 running parallel to the rails 48.

Figure 2:
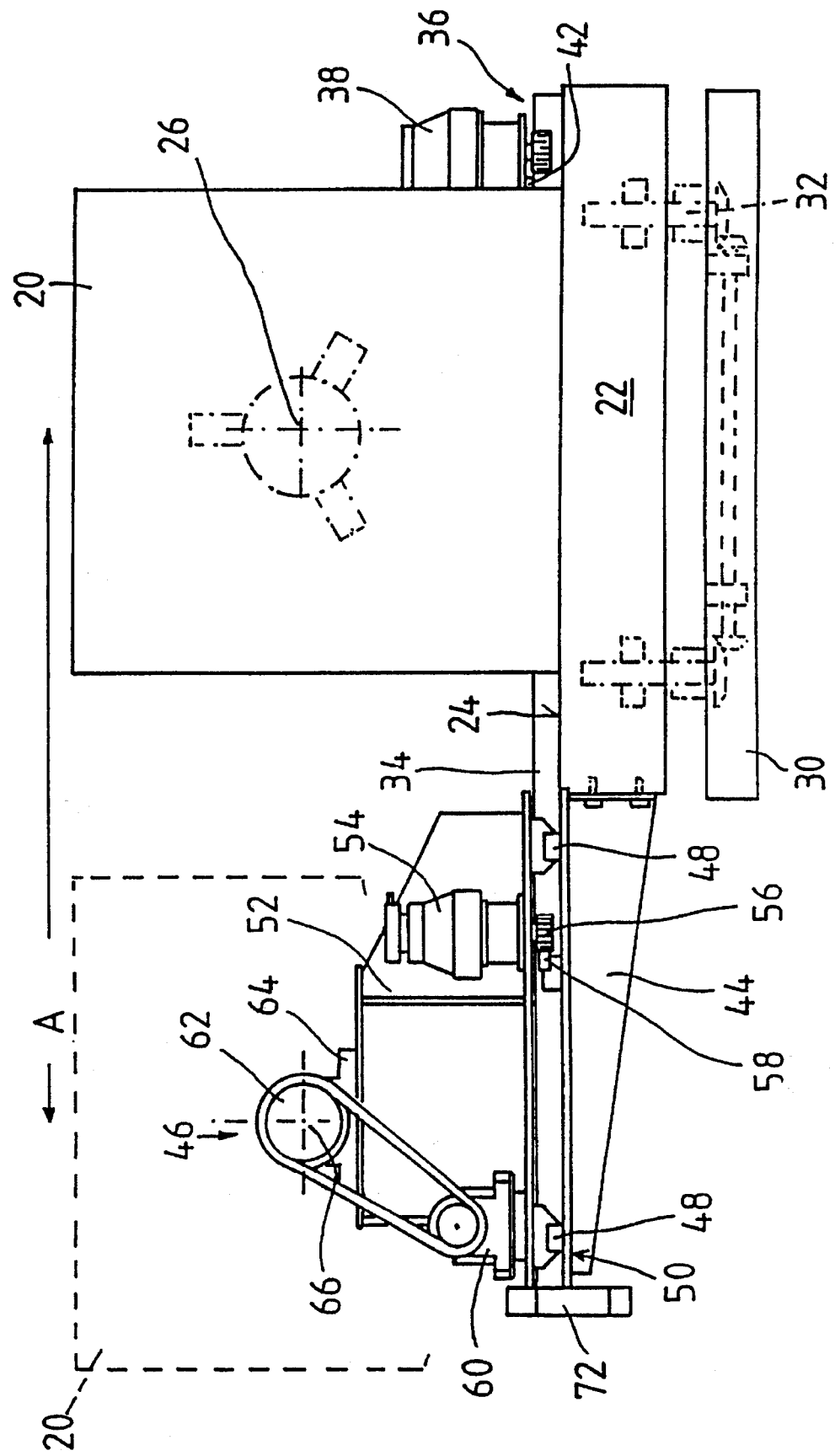
FIG. 2 is a representation of the test system shown in FIG. 1 viewed in the axial direction.

Still another rotary drive of the test-piece manipulator 46 is shown in FIGS. 1 and 2. For this purpose a drive motor 60 is provided which, by means of a gear chain, sets a body 62 of the test-piece manipulator 46 in revolution with a low number of revolutions per minute, e.g. 1 to 2 revolutions per minute. The body 62 of the test-piece manipulator is enclosed by two axially opposite rotor bearing blocks 64 which permit the described rotation of the body 62 about the axis of rotation 66, also called the axis of the test-piece manipulator 46. Finally the test-piece manipulator 46 has a mounting chuck 68 into which a test piece 70 is inserted as shown in FIG. 1.

As the figure shows, the rotor axis 26 and the axis of rotation 66 are at the same height above the surface 24. The rotor 20 must be moved the distance A in order to reach the service and adjustment position from the test position and vice versa.

The figures also show a cable pulling device 72 by means of which the sled 52 is supplied with electrical energy and compressed air if necessary; the control lines are also located in the cable pulling device 72.

The version shown in FIGS. 1 and 2 can be modified in numerous ways. Thus, for example, the test-piece manipulator 46 can be mounted not next to the rotor 20 as shown but axially displaced above the rotor 20. In this case, the rotor 20 of the first longitudinal guide can be vertically adjustable so that its axis can be inserted in the testing line and in the axis of rotation 66 of the test-piece manipulator. On the other hand, the rotor can also be attached in a stationary manner to the support platform 22 and the first longitudinal guide can make a lifting movement of the entire bracket 44 possible with respect to the support platform 22. In this case the first longitudinal guide along which said lifting movement takes place can be designed in the form of threaded spindles, hydraulic cylinders or the like which are positioned parallel to one another and on the support platform 22 at right angles to its surface 24.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:

1. Ultrasonic whole-body test system comprising;

a rotor being operable to mount a test probe and to receive an object to be tested, the rotor having a rotor axis and being coupled to a vertically adjustable support platform;

a manipulator operable to receive a calibration-piece, the manipulator having a manipulator axis and being coupled to the vertically adjustable support platform;

a longitudinal guide, which runs transversely to the rotor axis and the manipulator axis, the longitudinal guide being coupled between the support platform and at least one of the rotor and the manipulator such that the manipulator can move relative to the rotor between a rest position in which the rotor axis and the manipulator axis coincide and a service position in which the object to be rested can be received by the rotor.

2. Ultrasonic rotational test system in accordance with claim 1, wherein the longitudinal guide has at least one rail running in a horizontal plane.

3. Ultrasonic whole-body test system in accordance with claim 1, wherein the longitudinal guide runs at right angles to a surface of the support platform.

4. Ultrasonic whole-body test system in accordance with claim 1, further comprising adjustable stops coupled to at least one of the rail and the support platform.

5. Ultrasonic whole-body test system in accordance with claim 1, further comprising a base frame and a lifting and moving device, the lifting and moving device being coupled between the base frame and the support platform and being operable to adjust the vertical relation between the support platform and the base frame.

6. Ultrasonic whole-body test system in accordance with claim 1, further comprising a second longitudinal guide running in a direction parallel to the manipulator axis.

7. Ultrasonic whole-body test system in accordance with claim 1, further comprising a rotary drive mechanism coupled to the manipulator, the rotary drive mechanism being operable to rotate the calibration-piece about the manipulator axis.

8. Ultrasonic rotational test system comprising:

a rotor being operable to mount a test probe and to receive an object to be tested, the rotor having a rotor axis and being coupled to a vertically adjustable support platform;

a manipulator operable to receive a calibration-piece, the manipulator having a manipulator axis and being coupled to the vertically adjustable support platform;

an arm being coupled between the manipulator and a swivel, the swivel being coupled to the vertically adjustable support platform such that the arm is operable to swivel about a swivelling axis, the swiveling axis running parallel to the rotor axis and being equidistant from the rotor axis and the manipulator axis, the arm being operable to swivel between a test position in which the rotor axis and the manipulator axis coincide and a service position in which the object to be tested can be received by the rotor.

9. Ultrasonic whole-body test system in accordance with claim 8, further comprising adjustable stops coupled to the arm.

* * * * *

UNITED STATES PATENT AND TRADEMARK OFFICE
CERTIFICATE OF CORRECTION

PATENT NO. : 5,461,920
DATED : October 31, 1995
INVENTOR(S) : Reinhard Prause et al It is certified that error appears in the above-indentified patent and that said Letters Patent is hereby corrected as shown below:

Column 3, line 4, delete the word "min" and substitute therefor —mm—.
Column 5, Claim 1, line 16, delete the word "rest" and substitute therefor —test—.
Column 5, Claim 1, line 18, delete the word "rested" and substitute therefor —tested—.

Signed and Sealed this

Eighth Day of October, 1996

Attest:

BRUCE LEHMAN

*Attesting Officer*   *Commissioner of Patents and Trademarks*